United States Patent [19]

Dusemund et al.

[11] 3,996,242
[45] Dec. 7, 1976

[54] DITHIA-TETRAAZACYCLOOCTANE-TETRAOXIDES

[75] Inventors: Jürgen Dusemund, Berlin; Paul Richard Bock, Muenster, both of Germany

[73] Assignee: Chem. Pharmaz. Fabrik Dr. Hermann Thiemann GmbH, Luenen, Germany

[22] Filed: Nov. 14, 1975

[21] Appl. No.: 631,926

[30] Foreign Application Priority Data

Feb. 24, 1975 Germany .................... 2507879

[52] U.S. Cl. .................... 260/327 R; 424/277
[51] Int. Cl.$^2$ .................... C07D 285/38
[58] Field of Search .................... 260/327 R

[56] References Cited
UNITED STATES PATENTS 3,966,766  6/1976  Lehn .................... 260/327 R

*Primary Examiner*—Natalie Trousof
*Assistant Examiner*—C. M. S. Jaisle
*Attorney, Agent, or Firm*—Hugo E. Weisberger

[57] ABSTRACT

The present invention relates to novel 1,5-dithia-2,4,6,8-tetra-aza-cyclooctane-1,1,5,5-tetraoxides of the formula:

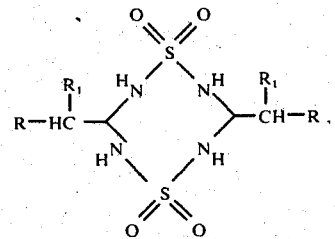

wherein
R represents halogen or a (lower) alkylsulphonyl radical,
$R_1$ represents hydrogen or chlorine.

The compounds according to the present invention exert valuable bacteriostatic, bactericidal, virostatic, cytostatic and immunosuppressive activities.

5 Claims, No Drawings

DITHIA-TETRAAZACYCLOOCTANE-TETRAOXIDES

The invention provides a 1,5-dithia-2,4,6,8-tetra-azacyclooctane-1,1,5,5-tetraoxide of the general formula I

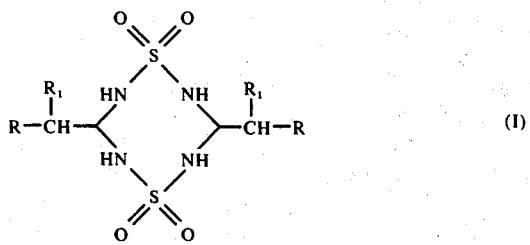

wherein each R denotes a halogen atom or a (lower) alkylsulphonyl radical and each $R_1$ denotes a hydrogen atom, or R and $R_1$ both denote chlorine atoms.

The dithia-tetra-aza-cyclooctane-tetraoxides of the general formula I have a bacteriostatic, bactericidal, virostatic cytostatic and/or immunosuppressive action. They are especially useful as disinfectants for external use; for example for disinfecting equipment and rooms. In combination with aldehydes, such as formaldehyde or glyoxal, the disinfecting effect, especially against Gram-negative germs, is intensified.

The invention also provides a process for the manufacture of a compound of the general formula I, which comprises treating sulphamide of the general formula II

$H_2N-SO_2-NH_2$   II.

with an acetaldehyde of the general formula III

or a dialkyl acetal thereof in which each alkyl moiety has up to 6 carbon atoms, in concentrated hydrochloric acid. Preferably, the reaction is carried out at room temperature, whilst stirring. The alkyl radicals in the acetal preferably have up to 4 carbon atoms, and an ethyl acetal or a methyl acetal is particularly preferred.

The invention further provides a pharmaceutical preparation which comprises a compound of the general formula I in admixture or conjunction with a pharmaceutically suitable carrier.

The compounds of the general formula I may be formulated in a conventional manner into unit dosage form, for example into tablets, dragees, capsules, syrups, suppositories, injections, ointments, creams, lotions and gels.

The dosage units and the daily doses are preferably as follows:

Unit dose oral: 5 — 50 mg
intravenous: 2 – 25 mg
Daily dose oral: up to 200 mg
intravenous: up to 100 mg.

The following Examples 1 and 2 illustrate the process of the invention, Examples 3 to 9 illustrate the preparation of pharmaceutical preparations in unit dosage form, and Example 9, the preparation of a disinfectant.

EXAMPLE 1

0.01 mole of sulphamide in 5 ml of concentrated hydrochloric acid are added to 0.012 mole of chloroacetaldehyde, at room temperature whilst stirring. After 5 minutes, the precipitate which has formed is filtered off and washed with ice water, dried and recrystallised from acetone/petroleum ether. 3,7-Di-(chloromethyl)-1,5-dithia-2,4,6,8-tetra-aza-cyclooctane-1,1,5,5-tetraoxide is obtained as colourless crystals of melting point 175° C (decomposition) in a yield of 70% of the theoretical yield.

EXAMPLE 2

0.01 mole of sulphamide in 5 ml of concentrated hydrochloric acid is added to 0.012 mole of bromoacetaldehyde-diethylacetal, at room temperature whilst stirring. After 5 minutes, the precipitate which has formed is filtered off and washed with ice water, dried and recrystallised from acetone/petroleum ether. 3,7-Di-(bromomethyl)-1,5-dithia-2,4,6,8-tetra-aza-cyclooctane-1,1,5,5-tetraoxide is obtained as colourless needle-shaped crystals of melting point 172° C (decomposition) in a yield of 60%.

When bromoacetaldehyde-dimethylacetal is used the yield is somewhat higher.

In the same way 3,7-di-(iodomethyl)-1,5-dithia-2,4,6,8-tetra-aza-cyclooctane-1,1,5,5-tetraoxide is obtained, as colourless needle-shaped crystals of melting point 162° C (decomposition), in a yield of 40% from iodoacetaldehyde-diethylacetal and sulphamide.

3,7-Di-(dichloromethyl)-1,5-dithia-2,4,6,8-tetra-aza-cyclooctane-1,1,5,5-tetraoxide can be obtained in the same way; discolouration above 180° C; melting point 212° C (decomposition).

EXAMPLE 3

| Tablets/dragees | |
|---|---|
| 3,7-Di-(chloromethyl)-1,5-dithia-2,4,6,8-tetra-aza-cyclooctane-1,1,5,5-tetraoxide | 20 mg |
| Lactose | 30 mg |
| Corn starch | 17 mg |
| Talc | 3 mg |

The active substance and lactose are granulated with isopropanol, the granules are mixed intensively with the remaining constituents and the mixture is pressed to give tablets or dragee cores. The cores are made into dragees by customary processes.

EXAMPLE 4

| Injection solution | |
|---|---|
| 3,7-Di-(bromomethyl)-1,5-dithia-2,4,6,8-tetra-aza-cyclooctane-1,1,5,5-tetraoxide | 10 mg |
| Polyethylene glycol, molecular weight 200 | 750 mg |
| Isotonic $NaC_1$ solution | to 3.0 ml |

The finely powdered active substance is dissolved in the 30% strength polyethylene glycol solution, whilst warming slightly and stirring, and after cooling the solution is made up to 3.0 ml with isotonic $NaC_1$ solution. The ampoules are sterile-filtered or sterilised.

EXAMPLE 5

| Ointment | | |
|---|---|---|
| Active substance according to Example 4 | | 1.0 g |
| Liquid paraffin | | 3.0 g |
| White petroleum jelly | to | 100.0 g |

The active substance is triturated with the paraffin and then dispersed in the white petroleum jelly at ambient temperature.

EXAMPLE 6

| Cream | |
|---|---|
| Active substance according to Example 4 | 1.0 g |
| Liquid paraffin | 32.0 g |
| Cetyl alcohol | 3.0 g |
| Anhydrous lanolin | 10.0 g |
| Cationic, complex, higher-alkylamine as softner | 2.0 g |
| Non-ionic sorbitane fatty acid ester as stabiliser | 2.0 g |
| Polyoxyethylene-sorbitane monostearate | 3.0 g |
| Preservative | 0.2 g |
| Distilled water | 46.8 g |

The active substance is dissolved in a small amount of water or triturated with a small amount of liquid paraffin. Cetylalcohol is melted with lanolin; liquid paraffin, softener, stabiliser and polyoxyethylene-sorbitane monostearate are added to the melt and the mixture is dissolved in the solution of the preservative in water at ambient temperature until a cream-like mass has formed. The solution or triturated form of the active substance is then admixed with the cream.

EXAMPLE 7

| Lotion | |
|---|---|
| Active substance according to Example 4 | 1.0 g |
| 94.6% strength ethanol | 15.0 g |
| Diethylene glycol monoethyl ester | 3.0 g |
| Citric acid | 0.2 g |
| Distilled water | 77.8 g |
| Glycerol | 3.0 g |

The active substance is dissolved in water or in the diethylene glycol monoethyl ether/ethanol mixture. Citric acid is dissolved in a small amount of water. The alcoholic phase and the aqueous phase are mixed together, glycerol is added and the lotion is mixed thoroughly.

EXAMPLE 8

| Gel | |
|---|---|
| Active substance according to Example 4 | 1.0 g |
| Carboxymethylcellulose (highly etherified) | 2.0 g |
| Glycerol | 30.0 g |
| 94.6% strength ethanol | 17.0 g |
| Distilled water | 50.0 g |

The active substance is dissolved in ethanol or water. The carboxymethylcellulose is triturated with glycerol and left to swell in water. The two phases are then homogeneously mixed.

EXAMPLE 9

1 g of 3,7-di-(bromomethyl)-1,5-dithia-2,4,6,8-tetra-aza-cyclooctane-1,1,5,5-tetraoxide is dissolved in 2,000 ml of water and surface are sprayed with this solution. The germs present on the surface (for example Staphylococcus sureus haemolyt). (Micrococcus pyogenes), Pseudomonas, Coli bacteria and Blastomyces) are killed within 1 to 2 hours.

The active substance can also be dissolved in dilute ethanol or isopropanol, instead of in water.

What we claim is:

1. A 1,5 dithia-2,4,6,8-tetra-aza-cyclooctane-1,1,5,5-tetraoxide of the formula:

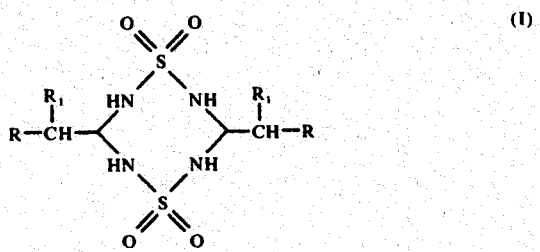

wherein
R is a halogen atom,
$R_1$ is selected from the group consisting of hydrogen and chlorine in which latter case R is also chlorine.

2. 3,7-Di-(chloromethyl)-1,5-dithia-2,4,6,8-tetra-aza-cyclooctane-1,1,5,5-tetraoxide.

3. 7-Di-(bromomethyl)-1,5-dithia-2,4,6,8-tetra-aza-cyclooctane-1,1,5,5-tetraoxide.

4. 3,7-Di-(iodomethyl)-1,5-dithia-2,4,6,8-tetra-aza-cyclooctane-1,1,5,5-tetraoxide.

5. 3,7-Di-(dichloromethyl)-1,5-dithia-2,4,6,8-tetra-aza-cyclooctane-1,1,5,5-tetraoxide.

* * * * *